US008388742B2

(12) United States Patent
Nunes

(10) Patent No.: US 8,388,742 B2
(45) Date of Patent: Mar. 5, 2013

(54) APPARATUS TO MEASURE PERMEATION OF A GAS THROUGH A MEMBRANE

(75) Inventor: Geoffrey Nunes, Swarthmore, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 66 days.

(21) Appl. No.: 13/004,232

(22) Filed: Jan. 11, 2011

(65) Prior Publication Data
US 2011/0168023 A1 Jul. 14, 2011

Related U.S. Application Data

(60) Provisional application No. 61/294,570, filed on Jan. 13, 2010.

(51) Int. Cl.
B01D 53/22 (2006.01)
(52) U.S. Cl. .................. 96/4; 95/43; 95/45; 96/6; 96/10
(58) Field of Classification Search ................ 95/25, 43, 95/45; 96/4, 417, 420, 421, 422, 6, 10
See application file for complete search history.

(56) References Cited

U.S. PATENT DOCUMENTS

| 3,241,293 | A | * | 3/1966 | Pfefferle | 95/56 |
| 3,604,246 | A | * | 9/1971 | Toren | 73/38 |
| 5,096,584 | A | * | 3/1992 | Reddy et al. | 210/321.74 |
| 5,361,625 | A | | 11/1994 | Ylvisaker | |
| 6,042,634 | A | * | 3/2000 | Van Tassel et al. | 95/14 |
| 7,117,720 | B2 | | 10/2006 | Bouten et al. | |
| 7,150,830 | B1 | * | 12/2006 | Katsube et al. | 210/321.8 |
| 7,169,213 | B2 | * | 1/2007 | Liu et al. | 96/4 |
| 7,257,990 | B2 | | 8/2007 | Bujas et al. | |
| 7,435,284 | B2 | * | 10/2008 | Piccinini et al. | 95/52 |
| 7,569,128 | B2 | | 8/2009 | Mayer et al. | |
| 2004/0244591 | A1 | * | 12/2004 | Edlund et al. | 96/11 |

* cited by examiner

Primary Examiner — Jason M Greene
Assistant Examiner — Anthony Shumate
(74) Attorney, Agent, or Firm — Kevin S. Dobson

(57) ABSTRACT

The present invention relates to an apparatus to measure permeation of a gas through a membrane. The membrane is mounted on a flange with two sealing areas. The region between the sealing areas defines an annular space. The annular space is swept with a gas in order to carry away any of the permeating gas which may leak through the sealing areas.

1 Claim, 3 Drawing Sheets

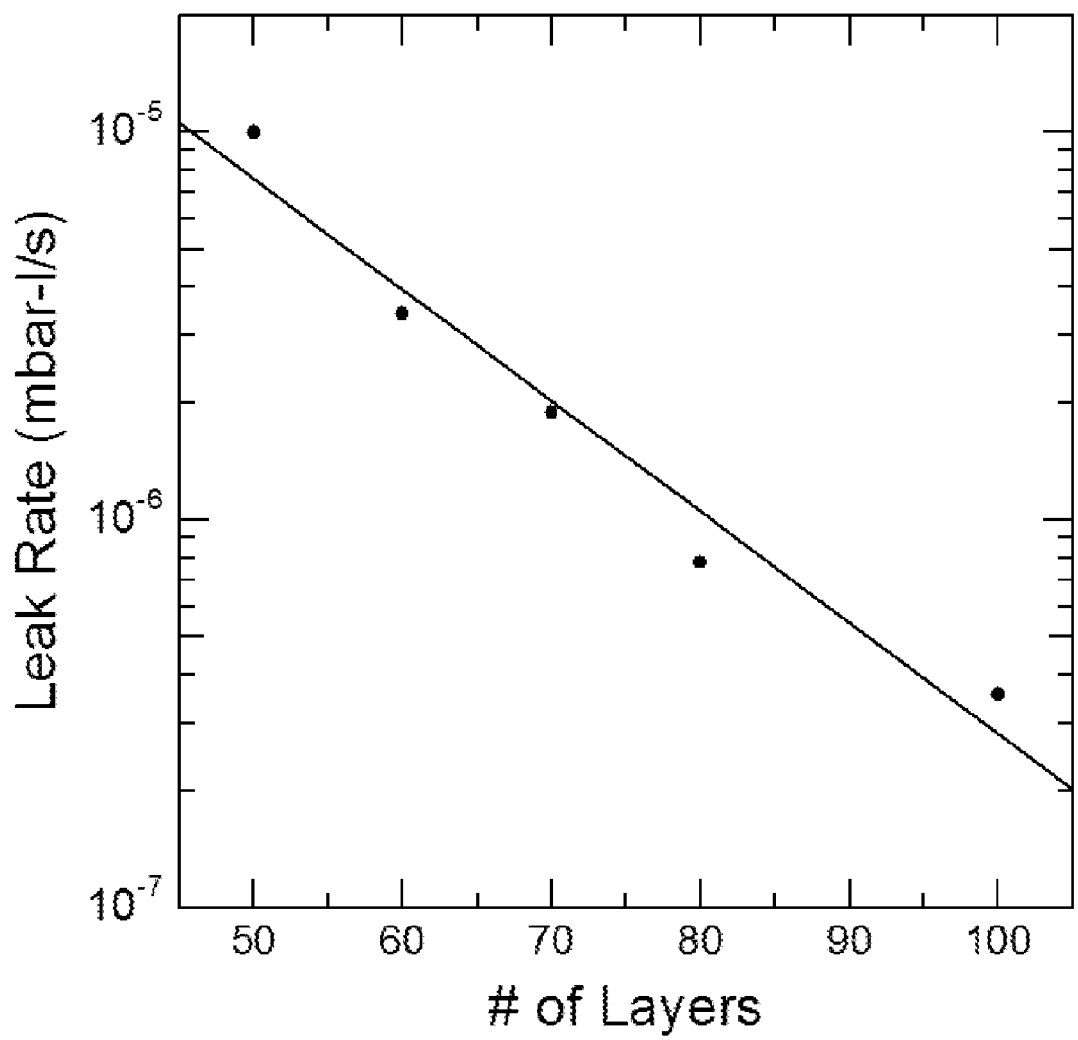
Figure 3 He transmission vs. number of ALD layers.

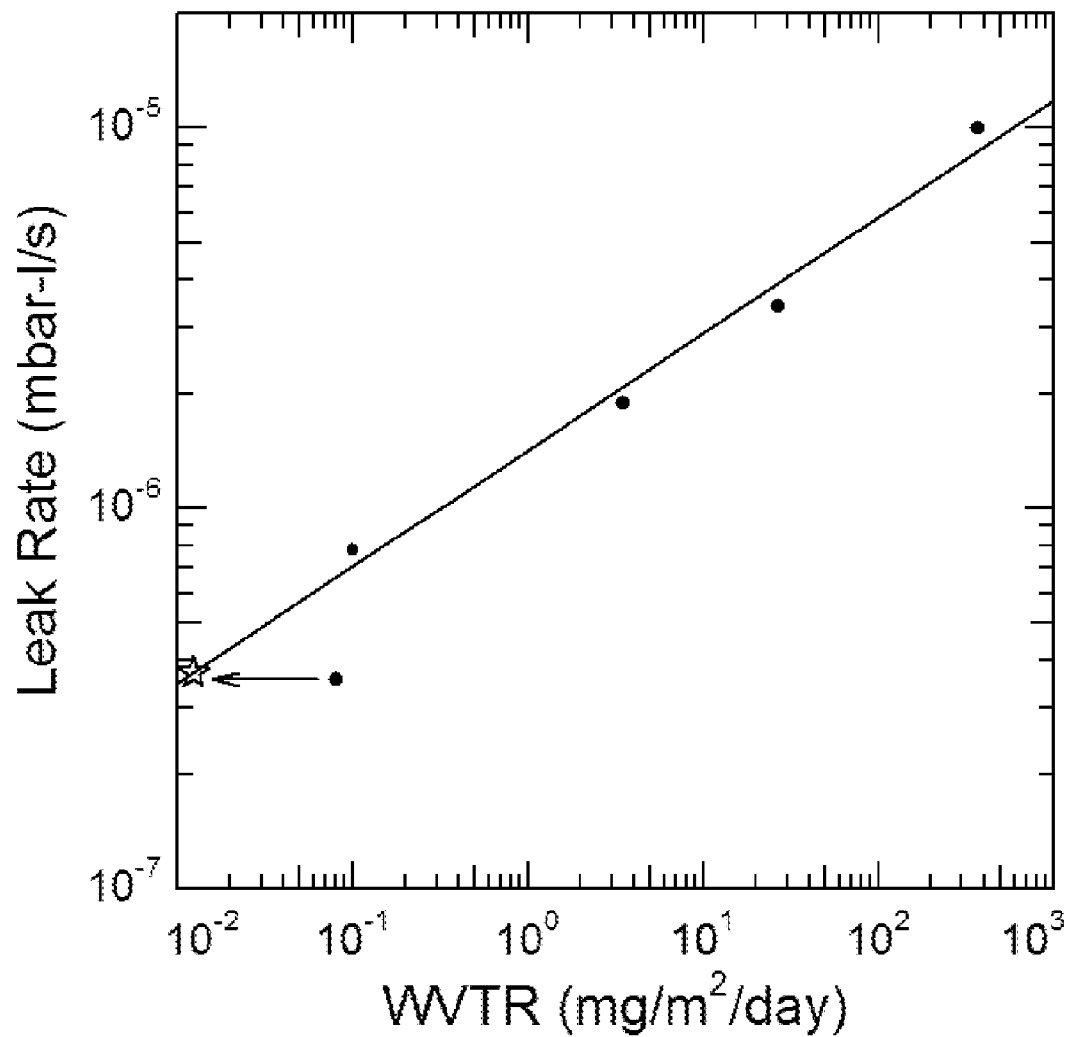
Figure 4  He transmission vs. historical WVTR.

APPARATUS TO MEASURE PERMEATION OF A GAS THROUGH A MEMBRANE

This invention was made with Government support under Contract No. DE-EE0000588.000 awarded by the Department of Energy. The Government has certain rights in this invention.

FIELD OF THE INVENTION

The present invention relates to an apparatus to measure permeation of a gas through a membrane.

TECHNICAL BACKGROUND

Current industry practice for evaluating ultrabarrier performance against water vapor transmission is to use a method that measures actual water transmission. These methods include coulometry (U.S. Pat. No. 7,569,128, MOCON, Inc.), detection of radioactive HTO (U.S. Pat. No. 7,257,990, General Atomics) and optical transmission through calcium (U.S. Pat. No. 7,117,720, Philips Electronics). All three of these approaches have severe limitations. They are all water based, and therefore inherently slow. The time required for establishment of steady state diffusion through a membrane is 5 to 10 times $t_s$, where $t_s=l^2/6D$. l is the thickness of the membrane, and D is the diffusivity of the permeant. In the case of water diffusing through PET, D is ~$4\times10^{-9}$ cm$^2$/s at 25 C, so that for a 5 mil (0.005 inch) thick membrane. The minimum measurement time is 10 to 20 hours. In practice, even longer measurement times are required, because the tests involve vapor transmission rates at or near the limit of sensitivity for each technique. Therefore, significant averaging is required to compensate for the poor signal to noise ratio. As a result, it takes on the order of 1 week to be confident that the transmission rate of an ultrabarrier is at or below the detection limit of either a coloumbic detection system or a radioactive tritium measurement. It takes even longer for the calcium test, because it takes a week or more for the measurement cell to achieve internal equilibrium and start to exhibit a steady state transmission rate.

In addition to their slow measurement rates, the above techniques are also limited in their sensitivity. According to product literature from MOCON® Minneapolis, Minn., the limit to their measurement technique is $5\times10^{-4}$ g/m$^2$/day. The limit of the calcium test is an order of magnitude lower: $5\times10^{-5}$ g/m$^2$/day. The requirement for an ultrabarrier layer for CIGS solar cells or OLED display devices is ~$10^{-6}$ g/m$^2$/day, making the tritium test, having a reported detection limit of $2\times10^{-7}$ g/m$^2$/day, the only technique sufficiently sensitive to verify performance at the required level. Even this test is not really sensitive enough, however, as efficient statistical sampling methods for process control require a continuous measure of the process, both in the out-of-limits and within-limits regimes. The HTO test could only provide such a measure for permeation rates that are just within the control limits, and in most cases could only provide a "pass/fail" type of response. The statistical requirements on "pass/fail" type measurements are so burdensome as to render process control essentially impossible.

The solution to the first limitation of these methods, the long measurement time, is to use an alternative test gas as a proxy for the water. Helium, for example, has a diffusivity in PET that is 500 times larger than that of water. As a result, $t_s$ for helium diffusing through a 5 mil membrane is about 15 seconds, resulting in a measurement time on the order of minutes. Such a substitution is a valid probe of the barrier properties, because permeation through an ultrabarrier occurs via micropores in the inorganic layer, rather than by permeation of the inorganic material itself. Once a correlation has been established between water vapor transmission and helium permeation for the bare PET (or other polymer) substrate, a rapid helium-based test can give a reliable value for the water vapor transmission rate (WVTR).

The required sensitivity for a test and measurement system based on the helium proxy principle is straightforward to estimate. The noise floor of the calcium test represents a reduction in WVTR over the bare substrate by a factor of 40000. From the permeation rate of helium through PET (~$2\times10^{-8}$ scc/cm/s/atm), and assuming a 10 cm diameter membrane and a driving pressure differential of 1 atm, this 40000 reduction factor gives a helium transmission rate of $3\times10^{-9}$ scc/s, well within the range of commercial helium mass spectrometer systems. To be useful as a process control technique, however, requires a sensitivity two orders of magnitude below that. Fortunately, state of the art, oil-free helium mass spectrometers are specified to have a sensitivity of $5\times10^{-12}$ scc/s which is three orders of magnitude below the calcium test limit.

Yilvisaker (U.S. Pat. No. 5,361,625) describes passage of gas through a membrane by exposing one side of the film to a test gas and exposing the other side of the film to a carrier gas.

In practice, however, measurements are limited by the background helium signal due to permeation through elastomer seals. Therefore, there is a need for an apparatus designed to hold ultrabarrier membranes for testing, while reducing or eliminating this background signal.

SUMMARY OF THE INVENTION

One aspect of the invention is an apparatus comprising
a) a membrane;
b) a pair of mating flanges supporting the membrane comprising an input flange and an output flange and an inner seal and an outer seal wherein an annular space is located between the inner and outer seal and wherein the input flange and the membrane define a gas input space and such that the output flange and the membrane define a boundary of the gas outlet space;
c) a purge gas inlet line connected to the annular space;
d) a purge gas outlet line connected to the annular space;
e) a test gas inlet line connected to the gas input space;
f) optionally, a test gas outlet line connected to the gas input space; and
g) a gas detection apparatus connected to the gas outlet space.

BRIEF DESCRIPTION OF THE DRAWINGS

FIG. 3 is a graph of He (helium) transmission vs. number of atomic layer deposition layers.

FIG. 4 is a graph of He (helium) transmission vs water vapor transmission rate.

DETAILED DESCRIPTION OF THE INVENTION

Figure 1:
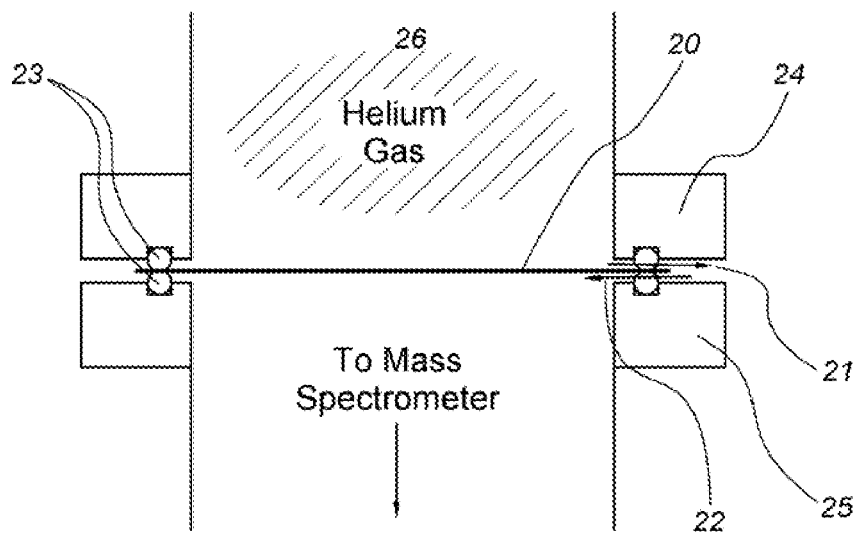
FIG. 1 is an illustration of a membrane under test, clamped between a pair of facing elastomer o-rings.

FIG. 1 illustrates a known embodiment of a test permeation apparatus utilizing a membrane (20) under test conditions. The membrane is clamped between a pair of facing elastomer o-rings (23) which are sealing areas. The o-rings are housed by an upper flange (24) and lower (25) flange. The upper chamber (26) contains He (helium) gas at a pressure of about 1 atmosphere. In a known embodiment the elastomer o-ring may be Viton which has a permeability to helium of ~9×10$^{-8}$ scc/cm/s/atm. For an apparatus that can test a 10 cm diameter area of barrier, helium gas will permeate out (21) of the upper chamber at a high rate: ~2.5×10$^{-3}$ scc/s. The back permeation (22) of the helium gas depends on the partial pressure of helium in the gap between the upper and lower flanges, which is in turn dependent on the geometry, in this instance, it is considered that the pressure is about 0.008 Torr (i.e. 1/100000 of the pressure in the helium upper chamber). The back-permeation of the helium gas will create a background signal of ~3×10$^{-9}$ scc/s. This signal is comparable to the signal that would be expected from a high performance membrane with a water vapor transmission rate (WVTR) of 10$^{-7}$ g/m$^2$/day. Measuring such a membrane with the apparatus shown in FIG. 1 would result in a poor signal to noise ratio of 1. The present invention builds on the apparatus described above and lowers the background signal created by back-permeation of the helium gas through the elastomer seals, and as a result improves the signal to noise ratio of the measurement of the permeation rate of gas directly through the membrane.

A solution to obtaining a lower background signal is to (a) add an outer annular seal to a test apparatus as described above, and have (b) an annular channel located between the inner annular seal and the outer annular seal. The annular channel will be continuously purged with a carrier gas (e.g. nitrogen) sweeping away helium that permeates through the inner annular seal. All other seals found in the test apparatus may be welded or metal-on-metal.

Figure 2:
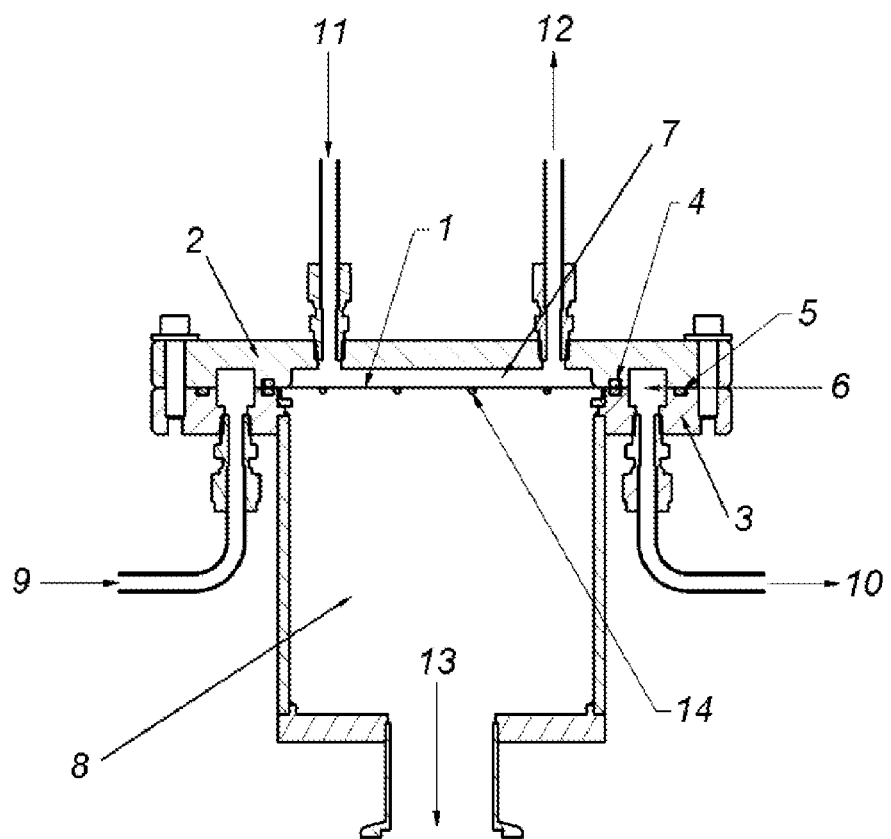
FIG. 2 is an illustration of a cross-section of a permeation apparatus.

As illustrated in FIG. 2, a cross-section of a test permeation apparatus is shown having a membrane 1. The membrane may be a polymer. The polymer may be selected from, but is not limited to, polyethylene terephthalate, polyethylene naphthalate, polyethylene tetrafluoride, ethylene tetrafluoroethylene, fluorinated ethylene propylene, polynorbornene, polyethersulfone, polycarbonate, or polyimide. The film may be coated with an inorganic coating or an inorganic and organic multi-layer coating to reduce permeation. The inorganic coating may be, but is not limited to, a metal oxide, metal nitride, metal carbide, metal oxynitride, metal oxyboride, or combination thereof, and may be applied by a number of deposition methods, including, but not limited to, atomic layer deposition, chemical vapor deposition, plasma enhanced chemical vapor deposition, sputtering, electron beam evaporation, or thermal evaporation. In multilayer coatings, the organic component may be, but is not limited to, low molecular weight or monomeric acrylates or silicones. The organic layers may or may not be cross-linked after application by, for example, ultraviolet radiation or plasma methods. A pair of mating flanges, an input flange 2 and an output flange 3 support the membrane 1. The pair of flanges have an inner seal 4 and outer seal 5. The inner seal 4 and outer seal 5 define an annular space 6 between the inner seal 4 and outer seal 5. The input flange 2 and the membrane 1 define a gas input space 7. The output flange 3 and the membrane 1 define a gas outlet space 8. A purge gas inlet line 9 and outlet line 10 are connected to the annular space 6. A test gas inlet line 11 is connected to the gas input space. Optionally, a test gas outlet line 12 is connected to the gas input space 7. A gas detection apparatus 13 is connected to the gas outlet space 8. The gas detection apparatus 13 may be a mass spectrometer or an ionization gauge. The membrane 1 may be supported by a support screen 14, which may be in the form of a woven wire screen, or porous metal, ceramic, or glass frit.

EXAMPLES

Example 1

Helium transmission rates were measured on PET films with $Al_2O_3$ films deposited by atomic layer deposition (ALD). The He transmission was compared with typical WVTR data for similar films.

Five membranes (sample numbers A-E) were supplied, with criteria indicated in the following table 1:

TABLE 1

Samples for measurement

| Sample Number | # of ALD layers | typical WVTR (mg/m$^2$/day) |
|---|---|---|
| A | 50 | 370 |
| B | 60 | 26.6 |
| D | 70 | 3.5 |
| E | 80 | 0.1 |
| C | 100 | .08 |

Helium Transmission Measurement Procedure

Helium transmission measurements were made in a test apparatus (similar to the embodiment illustrated in FIG. 2) using a Leybold UL200 portable leak detector. This instrument has an internal calibration source of unknown age, so the absolute calibration is unknown. Also, the scale-to-scale linearity of the instrument is unknown at this point.

Measurements were made using the following procedure.
1. The membrane was placed on the output flange of the apparatus, and the input flange was fastened down.
2. Nitrogen gas was used to raise the pressure above the film to ~800 Torr so that the film was in good contact with the support screen.
3. The leak detector was engaged to evacuate the lower chamber.
4. With the pressure in the lower chamber in the 10$^{-3}$ mbar range, the atmosphere found in the input space located above the membrane was removed with a rotary vane roughing pump.
5. The system was allowed to remain in this state for 10 to 20 minutes until a steady baseline helium leak rate was observed.
6. Helium gas was admitted into the input space to a pressure of ~900 Torr.
7. The leak rate was allowed to stabilize (10 to 20 minutes), and was recorded in Table 2.

Results

TABLE 2

He transmission measurements

| Sample # | He Trans. Rate. (mbar l/s) | He Pressure (Torr) | Baseline (mbar l/s) |
|---|---|---|---|
| A | 1.0 × 10$^{-5}$ | 911 | 1.9 × 10$^{-9}$ |
| B | 3.4 × 10$^{-6}$ | 908 | 9.0 × 10$^{-9}$ |
| D | 1.9 × 10$^{-6}$ | 910 | 6.4 × 10$^{-9}$ |
| E | 7.9 × 10$^{-7}$ | 914 | 9.3 × 10$^{-9}$ |
| C | 3.6 × 10$^{-7}$ | 910 | 4.7 × 10$^{-9}$ |

Analysis

FIG. 3 shows He transmission vs. number of layers. The raw data were adjusted as follows $$\text{He rate} = (\text{raw rate} - \text{baseline}) \times \frac{910\ Torr}{\text{He pressure}}.$$

FIG. 4 shows the same He (helium) transmission data as shown in FIG. 3, but plotted vs. the typical WVTR numbers given in Table 1. The star symbol plotted in FIG. 4 represents the value the 100 layer sample might be expected to read if the WVTR data tracked the He rate instead of hitting the MOCON vapor transmission instrument noise floor.

What is claimed is:

1. An apparatus comprising:
a) a membrane having an input surface, an output surface and a peripheral edge;
b) a housing including a pair of mating flanges supporting the membrane,
one flange being an input flange and the other flange being an output flange,
the input flange and the input surface of the membrane cooperating to define a gas input space, the housing having a test gas inlet that communicates with the gas input space,
the output flange and the output surface of the membrane cooperating to define a gas outlet space, the housing having a test gas outlet that communicates with the gas output space;
wherein the improvement comprises:
an inner seal and an outer seal mounted between the input and the output flanges, the inner seal being disposed closer to the peripheral edge of the membrane than the outer seal,
the input flange and the output flange cooperating to define an annular space therebetween, the annular space being disposed between the inner and the outer seals, and
a purge gas inlet line and a purge gas outlet line both connected to the annular space.

* * * * *